Figure 1A:

United States Patent [19]

Alberti et al.

[11] Patent Number: 4,826,663

[45] Date of Patent: May 2, 1989

[54] ZIRCONIUM PHOSPHATE AND METHOD FOR ITS PREPARATION

[75] Inventors: Giulio Alberti, Perugia; Francesco Bartoli, Rome; Umberto Constantino, Perugia; Francesco Di Gregorio, Rome; Claudio Valentini, Rome, all of Italy

[73] Assignee: Eniricerche S.p.A., Milan, Italy

[21] Appl. No.: 862,809

[22] Filed: May 13, 1986

[30] Foreign Application Priority Data

May 15, 1985 [IT] Italy .............................. 20716 A/85

[51] Int. Cl.[4] .................. C01B 15/16; C01B 25/26
[52] U.S. Cl. .................................. 423/157; 423/181;
423/308; 423/659; 502/208; 556/24; 556/26
[58] Field of Search ............... 423/309, 311, 308, 157,
423/181, 659; 502/208; 556/24, 26

[56] References Cited

U.S. PATENT DOCUMENTS 3,416,884 12/1968 Stynes et al. .................. 423/309
4,025,608 5/1977 Tawil et al. .................. 423/311
4,381,289 4/1983 Nowell et al. .................. 423/311

FOREIGN PATENT DOCUMENTS 983211 2/1965 United Kingdom ............... 423/311

OTHER PUBLICATIONS

Yu I. Sukharev, "Cationic Application of Ion-Exchange Zirconium Phosphates", *Inorganic Materials*, vol. 10, No. 3, pp. 427–430, Mar. 1974 (published Aug. 1974).

*Primary Examiner*—John Doll
*Assistant Examiner*—Wayne A. Langel
*Attorney, Agent, or Firm*—Hedman, Gibson, Costigan & Hoare

[57] ABSTRACT

The invention relates to a zirconium phosphate in particles having sizes comprised within the range of from 1 to 100 $\mu$m, a lamellar structure with interlayer distance, in the anhydrous state, comprised within the range of from 7.9 to 8.2 Å and a surface area comprised within the range of from 9 to 20 m$^2$/g.

The method consists in altering the lamellar structure of a zirconium phosphate with layer structure of alpha type by intercalating into it an organic substance containing a proton-acceptor group and water and by a treatment with ultrasounds, in regenerating the hydrogen form of said zirconium phosphate by an acid and in washing the same with diluted acids and/or water.

25 Claims, 2 Drawing Sheets

ZIRCONIUM PHOSPHATE AND METHOD FOR ITS PREPARATION

The present invention relates to a particular type of zirconium phosphate and to the method for its preparation.

One among the most widely used and studied ion exchangers belonging to the class of acid salts of tetravalent metals is zirconium phosphate with layer structure of alpha type [A. Clearfield, Inorganic Ion Exchange Materials, C.R.C. Press, Boca Raton (FA) USA, 1982].

Such an ion exchanger has been obtained by two different preparation methods.

In the first method, known as the "reflux method", zirconium phosphate is first prepared in the amorphous state, and the product is then made crystallize by refluxing it in aqueous solutions of phosphoric acid [A. Clearfield and J. A. Stynes, J. Inorg. Nucl. Chem. 26, 117 (1964)]. The degree of crystallinity increases with the reflux time, and with the reflux time being the same, it increases with increasing concentration of the solution of phosphoric acid. Parallely to the crystallinity degree the crystal sizes increase. In order to obtain microcrystals having dimensions of $\mu m$ order and a good crystallinity degree, reflux times longer than 100 hours in 10–12M phosphoric acid are required.

In the second method, also known as the "method by direct precipitation in the presence of HF", a solution is first prepared containing a zirconium-(IV) fluorocomplex in phosphoric acid [G. Alberti, E. Torraca, J. Inorg. Nucl. Chem. 30, 317 (1968)]. The crystalline zirconium phosphate is then made precipitate by decomposing the fluorocomplex by slowly evaporating hydrofluoric acid. In this method, the cristallinity degree and the crystal dimensions depend on the speed with which hydrofluoric acid has been evaporated off. If the evaporation is controlled in such a way that the precipitation may occur during a time longer than 24 hours, optimum crystallinity degrees and particles having sizes of from some tens to some hundreds of $\mu m$ are obtained.

By slow thermal decomposition of zirconium fluorocomplexes even crystals having sizes of some mm can be obtained G. [Alberti, U. Costantino, R. Giulietti, J. Inorg. Nucl. Chem., 42, 1062 (1980)].

Independently from the preparation method, the zirconium phosphate having layer structure of alpha type has the composition: $Zr(HPO_4)_2 \cdot H_2O$ and an interlayer distance of 7.6 Å. The water molecule is easily lost by heating to 110° C. with decrease of the interlayer distance from 7.6 Å to 7.4 Å.

The dehydration is irreversible in the sense that the anhydrous zirconium phosphate cannot be re-hydrated even by dipping it into water. The crystalline structure of $\alpha$-$Zr(HPO_4)_2 \cdot H_2O$ is presently known [A. Clearfield and G. D. Smith, Inorg. Chem., 8, 431 (1969)].

The arrangement of $\equiv$P-OH groups is such that in the interlayer region cavities are formed (one cavity per each zirconium atom) connected by windows though which ions or molecules having a cross-section lower than or equal to that of potassium ion can easily pass, whilst larger species, such as $Rb^+$, $Cs^+$, $Ba^{2+}$ or large organic ions cannot enter due to steric reasons.

It has been surprisingly found that a type of zirconium phospate allows the passage and hence the intercalation and/or the exchange of ions larger than potassium, thus overcoming the disadvantages of the prior art.

The zirconium phosphate according to the invention is in the hydrogen form and. has particles having dimensions comprised within the range of from 1 to 100 $\mu m$, a lamellar structure with interlayer distance in the anhydrous state comprised within the range of from 7.9 Å to 8.2 Å and a surface area comprised within the range of from 9 to 20 $m^2/g$.

The method for the preparation of the zirconium phosphate according to the invention comprises:

(a) the intercalating into a crystalline zirconium phosphate $\alpha$-$Zr(HPO_4)_2 \cdot H_2O$ having interplanar distance d=7.6 Å of an organic substance contaning an proton-acceptor group and water up to obtain a stable colloidal aqueous suspension of said intercalated Zr phosphate;

(b) the treatment of the colloidal suspension with ultrasounds, then with acids, preferably mineral acids, not zirconium-complexing, in particular selected from HCl, $H_2SO_4$ and $HNO_3$, for the regeneration of the hydrogen form, with the formation of a precipitate of zirconium acid phosphate with modified lamellar structure;

(c) the separation of precipitate from mother liquors, and the washing of th same with diluted acids, preferably mineral acids, and/or water.

According to a preferred form of embodiment of the method according to the present invention, the treatment with ultrasounds is continued until the optical density of the suspension remains constant and is no longer influenced by said treatment with ultrasounds.

It should be observed that the zirconium acid phosphate having modified lammelar structure obtained according to the invention and hereunder indicated also as "delaminated-ZPH", has properties of exchange, intercalation and absorption very different from those of the materials of the prior art on the basis of lamellar zirconium phosphate with layer structure of alpha type.

As the organic substance containing proton-acceptor groups, an amine is preferably used and this is preferably selected between methylamine and n-propylamine.

In the following, reference is made to this latter for easiness' sake, and the phenomena which can be evidenced during the process of the invention are explained.

The crystals of $\alpha$-$Zr(HPO_4)_2 \cdot H_2O$ are dispersed in water and n-propylamine is added to the dispersion under mechanical stirring. For example, the amount of propylamine can be varied within the range of from 25% to 75% (preferably 50%) of the number of gram-atoms of acidic protons present in the $\alpha$-$Zr(HPO_4)_2 \cdot H_2O$ amount used; usually, n-propylamine is added at a slow addition rate, but the addition modalities are not crytical. Also the ratio between the amount of crystals and the amount of water used can be varied within a wide range, from a minimum of 0.05 g per 100 g of water up to a maximum value which is essentially a function of the stirring system used and of its efficiency. In fact, while the amine is being progressively added, the mixture viscosity tends to increase, and the higher the zirconium phosphate/water ratio, the greater such an increase in viscosity. The modification in lamellar structure caused by the intercalating of n-propylamine is such, that a very stable colloidal suspension is even formed. Such a suspension can be obtained also by causing the intercalation to take place in a non-aqueous medium (e.g., in an alcohol, in particular in methanol)

and then adding water. The suspension of zirconium phosphate with modified lamellar structure obtained by intercalation in water or by dispersion in water of the intercalated product previously prepared in a non-aqueous medium is used for the treatment with ultrasounds.

The regeneration of zirconium phosphate in hydrogen form is carried out by acidifying the colloidal suspension up to a pH value comprised within the range of from 0 to 3, preferably to pH 1. The acidification causes also the flocculation of zirconium acid phosphate, which can be recovered by simple filtering, and washing and drying in air at room temperature or by spray-drying or freeze-drying.

Differently from $\alpha$-$Zr(HPO_4)_2 \cdot H_2O$ (d=7.6 Å, the product according to the present invention exchanges quickly such large-sized ions as $Cs^+$ and $Ba^{2+}$, and is furthermore able to absorb amines, alcohols and organic cations of even large size from aqueous or organic solutions. In general, the product according to the present invention can be used as absorbent and intercalating agent for proton-acceptor organic substances having molecular weights up to 500 Daltons.

For example, the absorption of $Cs^+$ ion from an 0.1M CsCl aqueous solution maintained at pH=3 is of 1.25 meq/g, that of methylene blue from aqueous solution arrives up to 1.85 meq/g, bornylamine and quinine can be accomodated inside the interlayer region, whilst alcohols are even intercalated by the exchanger also by simple cold washing with them.

The dry product has also the property of considerably hydrating when it is contacted with water, with formation of $\alpha$-$Zr(HPO_4)_2 \cdot nH_2O$, the value of n of which depends on the relative humidity under which the sample is conditioned. The hydration causes an increase of the interplanar distance, which can be easily detected by the powder X-ray diffraction spectrum. For example, a sample conditioned under a relative humidity of 92% has increased its interlayer distance up to 10.1 Å, and n has resulted equal to 3.5.

In some samples the hydration is so high that when they are placed in water, they swell up to yield a gelified mass showing an X-ray diffraction spectrum similar to that of the amorphous substances. However, by carrying out a gradual drying, it has been found, by controlling the X-ray diffraction spectrum of the samples, that the gradual reappearance occurs of the peaks typical of the phases with lower hydration degree, until finally the anhydrous compound having an interlayer distance comprised within the range of from 7.9 to 8,2 Å is obtained. Such a behaviour would let think that the interlayer distance of the samples dipped into water may reach even larger values than those obtained by the conditioning under relative moisture of 92% (10.1 Å).

It should be observed that the method according to the present invention leads also to the obtainment of powders constituted by particles the planar dimensions of which are of the same order of magnitude as of the initial $\alpha$-$Zr(HPO_4)_2 \cdot H_2O$ crystals, whilst the thickness, due to the modification occurred in the lamellar structure, is considerably lower (from 10 to 200 times as lower).

As a consequence, the surface area of delaminated-ZPH according to the present invention is considerably larger than that of crystalline zirconium phosphate $\alpha$-$Zr(HPO_4)_2 \cdot H_2O$ being used as the starting material. By starting for example from crystals having sizes of some tens of $\mu$m and surface areas of 0.1–0.2 $m^2/g$, products with surface areas of 9–20 $m^2/g$ can be obtained.

The combination of a high surface area with particles having considerable planar distances is a typical characteristic of delaminated-ZPH according to the present invention and such a characteristic, besides to the purpose of the surface absorption of various polar substances, can be advantageously used in all catalytic processes in which zirconium phosphate is used, both as catalyst and as catalyst support.

Some examples are now supplied to the purpose of better illustrating the invention, it being understood that the invention must not be considered as limited to them or by them.

Because the number of equivalents of acidic protons present per g of delaminated-ZPH depends on the hydration degree, which depends in its turn on the relative humidity under which the sample has been conditioned, in the following examples the absorption capacity, for comparison homogeneousness' sake, is referred, unless otherways specified, to 1 g of anhydrous product.

EXAMPLE 1

Zirconium phosphate with layer structure of alpha type has been prepared by the method of direct precipitation in the presence of hydrofluoric acid. In particular, 85 g of $ZrOCl_2 \cdot 8H_2O$ was dissolved in 1.2 l of water. To the solution first 80 ml of concentrated solution at 40% by weight of HF and then 715 ml of phosphoric acid at 85% by weight were added. The clear solution placed in a plastics vessel was heated in water bath at 80° C. and into it pre-humidified air was bubbled. The complete precipitation was reached over a time of about 4 days. The crystals were separated from the solution, washed with distilled water up to pH 4–4.5 and stored in dryer over phosphoric anhydride.

One gram of $\alpha$-$Zr(HPO_4)_2 \cdot H_2O$ (prepared as above said) with average crystal size around 15 $\mu$m and surface area of 0.2 $m^2/g$ was suspended in 100 ml of water, and 50 ml was added of an 0.066 M n-propylamine aqueous solution. The additions was carried out slowly, dropwise during about 4 hours under vigorous stirring. By keeping the mixture stirred for further about 20 hours a colloidal suspension of product with modified lamellar structure was obtained. This suspension was treated with ultrasounds (frequency of 7 MHz and power of 150 W) for a total time of 14 minutes. The ultrasound treatment was carried out by alternating 2 minutes of treatment to one minute of rest interval, during which the vessel was cooled by dipping into water. After this treatment, the optical density of the suspension at 620 nm varied from the initial value of 0.41 to an end value of 0.10. The solution was then acidified with 6 M HCl up to pH 0.7. The so-obtained precipitate was filtered off, washed three times each time with 100 cc of 0.1 M HCl, and finally with water until the washing liquors reached a pH$\geq$3.5. To the moist product obtained water was added up to a total volume of 60 ml, and stirred, to obtain a suspension which was poured by small portions into liquid nitrogen. The frozen granules were freeze-dried. The solid product obtained was further dried at 70° C. and under a pressure of 15 $mm_{Hg}$ (End yield 0.96 g).

The obtained product, after conditioning at room temperature over phosphoric anhydride, had an interlayer distance, measured from the powder X-ray dispersion spectrum, of 8.1 Å. (It should be observed that during the determination of the diffraction spectrum the sample must be protected against atmospheric humidity, otherways phenomena of rehydrating occur, which cause an increase of the interlayer distance).

The surface area of the product, computed from the nitrogen absorption data by the T.B.E. theory, was of 19 m$^2$/g.

Figure 1B:

In FIG. 1A a photomicrograph of the product obtained by a scanning electron microscope (Philips Mod. 501/B) at 791× magnification, and in FIG. 1B the photomicrograph of the same product at 6330× magnification is reported. In the two photomicrographs the white segments represent 10 μm and 1 μm respectively. From the two photomicrographs the dimensions and the morphological characteristics of the individual particles can be easily seen.

The absorption power of the product for methylene blue from aqueous solution has resulted of 1.1 mmol of dye per g of product.

EXAMPLE 2

One gram of α-Zr(HPO$_4$)$_2$.H$_2$O of Example 1 was suspended in 50 ml of water and to it 25 ml of 0.13 M n-propylamine aqueous solution was added. The addition modalities and all other operations were carried out exactly as described in Example 1. The end yield in dry delaminated-ZPH was of 0.97 g, its interlayer distance (at room temperature and under relative humidity=60%) was of 8.7 Å. Its absorption power for methylene blue was of 1.2 mmol/g.

EXAMPLE 3

The process was carried out exactly as described in Example 2, with the dfference that the recovery of the product in the dry state was carried out by spray-drying. The yield was of 0.8 g, the interlayer distance of the product obtained under the same conditions as of Example 2 was of 8.6 Å, and the absorption power for methylene blue was of 0.9 mmol/g.

EXAMPLE 4

The process was carried out exactly as described in Example 2. The recovery of the end product in the dry state was carried out by direct drying of the moist product at 70° C. and under a pressure of 15 mm$_{Hg}$.

The yield was of 0.92 g, the interlayer distance was of 8.8 Å, (relative humidity of 60%) and the absorption power for methylene blue of 1.3 mmol/g.

EXAMPLE 5

One gram of α-Zr(HPO$_4$)$_2$.H$_2$O, the same sample as of Example 1, was suspended in 50 ml of absolute methanol containing 0.28 ml (0.0033 mol) of n-propylamine and was kept under stirring for about 10 hours.

The intercalary-amine containing product, after filtering and drying, was suspended in 150 ml of water and stirred for 30 minutes. The so-obtained colloidal suspension was submitted to treatment with ultrasounds by the same modalities as described in Example 1. The optical density of the ultrasound-treated end solution was of 0.099 at 620 nm. By proceeding exactly as described in Example 1, 0.94 g of product having and interlayer distance of 8.6 Å (relative humidity=60%) and an absorption power for methylene blue of 0.9 mmol/g of product conditioned over P$_2$O$_5$ was obtained. The surface area of this product (T.B.E.) was of 15 m$^2$/g.

EXAMPLE 6

An amount of 1.000 g of product obtained according to as described in Example 1 was brought to constant weight in vacuum dryer over phosphoric anhydride and subsequently equilibrated over saturated solutions of magnesium nitrate [relative humidity (R.H.) 60%], of sodium chloride (R.H. 75%), and barium chloride (R.H. 92%). The following % weight increases and the following values of interlayer distance were recorded:

| R.H. | % Weight Increase | d (Å) |
| --- | --- | --- |
| ~0 | 0 | 8.1 |
| 60 | 7.9 | 8.6 |
| 75 | 14.1 | 9.4 |
| 92 | 17.5 | 10.1 |

The sample reconditioned over phosphoric anhydride returned back to its starting weight of 1.000 g.

Another sample of 0.284 g of delaminated-ZPH, prepared according to Example 2, stored in air (R.H.=60%), dried in oven at 150° C. for 24 hours showed a weight loss of 7.6%. This dry product, kept resting in air on the analytical balance returned to its initial weight within a time of about 2 hours.

EXAMPLE 7

One gram of zirconium phosphate with modified lamellar structure and conditioned over P$_2$O$_5$ prepared as described in Example 2 was dispersed with strong stirring in 100 ml of 0.100 M CsCl solution having pH=3.00.

An immediate decrease was observed in solution pH which, about 1 minute after the addition of delaminated-ZPH resulted equal to 1.79. To the purpose of raising the solution pH to the value of 3.00, 12.5 ml of a 0.100 M CsOH solution was added. It can be inferred that under these conditions 1 g of delaminated-ZPH exchanges 1.25 mmol of its acidic protons with 1.25 mmol of Cs$^+$.

The same test has been carried out by using 1 g of α-Zr(HPO$_4$)$_2$.H$_2$O (starting material of Example 1 used to obtain the delaminated-ZPH). In this case, no appreciable changes were observed in solution pH and hence no absorption of Cs had occurred.

EXAMPLE 8

One gram of delaminated-ZPH conditioned over P$_2$O$_5$ prepared as described in Example 2 was dispersed under strong stirring in 150 ml of a 0.050 M BaCl$_2$ solution having pH=5.25.

An immediate decrease was observed in solution pH which, about 1 minute after the addition, resulted equal to 1.75. The analysis of the supernatant solution for Ba contents showed the presence of residual 6.45 mmol of Ba$^{++}$ ions, as compared to the 7.50 mmol initially present. It can be inferred that under these conditions 1 g of delaminated-ZPH exchanges 2.1 mmol of its acidic protons with 2.1 mmol of Ba$^{++}$ ions.

EXAMPLE 9

One g of α-Zr(HPO$_4$)$_2$.H$_2$O was treated according to as described in Example 1, until the colloidal solution was obtained. This latter, after having undergone the treatment with ultrasounds was acidified. The obtained precipitate was washed first with 0.1M HCl and then with water according to as described in Example 1. The moist product which was obtained was washed three times with absolute ethanol.

Its interlayer distance resulted to be of 14.2 Å, similar to that of crystalline zirconium phosphate with two intercalary alcohol molecules.

Another aliquot of the product was washed with n-propyl alcohol (three times). In this case, the moist product showed on X-ray analysis an interlayer distance of 16.6 Å, similar to that of the intercalation compound $Zr(HPO_4)_2 \cdot n$-propanol [U. Costantino, J. Chem. S. Dalton, 402 (1979)].

EXAMPLE 10

One g of $\alpha$-$Zr(HPO_4)_2 \cdot H_2O$ underwent the lamellar structure modification, was ultrasound-treated and washed according to as described in Example 1, until the moist product was obtained. This latter was dispersed again in water up to a total volume of 100 ml. This suspension was analyzed for its contents in zirconium phosphate by drawing, under stirring, 5-ml portions, which, placed inside weighing bottles, were kept at 70° C. and under a pressure of 15 $mm_{Hg}$ until the most of water had evaporated off, and finally were conditioned to constant weight over phosphoric anhydride in vacuum dryer. The contents of the suspension, so determined, resulted equal to 9.5 mg of anhydrous material per ml.

To 10 ml of suspension 25 ml was added of a 0.0102M aqueous solution of methylene blue (equivalent to 0.255 mmol). After letting the equilibrium to be reached under stirring for 48 hours, the supernatant solution was analyzed for its contents in methylene blue. Such contents resulted of residual 0.088 mmol.

It can be inferred that the product had absorbed 1.85 mmol of dye per g of product conditioned over phosphoric anhydride.

EXAMPLE 11

To 15 ml of the aqueous suspension of Example 10, containing 142.5 mg of anhydrous product, 55 ml of absolute ethanol and 30 ml of a 0.073M solution of bornylamine in alcohol were added.

After 24 hours of equilibration, 10 ml of supernatant solution was drawn and titrated with 3.16 ml of 0.05M HCl, from which it can be inferred that the intercalary bornylamine was equal to 4.28 mmol/g.

EXAMPLE 12

To 8 ml of the aqueous suspension of Example 10, containing 76 mg of anhydrous product, 89.5 ml of absolute ethanol and 2.5 ml of a 0.052N solution of quinine in alcohol were added.

After 24 hours of contact time, the supernatant solution was analyzed for its contents in residual quinine.

Such a contents resulted equal to 0.0809 mmol as compared to the 0.130 mmol initially added to react. It can be inferred that the product capacity to absorb quinine was equal to 0.31 mmol of quinine per g.

We claim:

1. Particulate zirconium acid phosphate of modified lamellar structure having a particle size of from 1 to 100 μm, a lamellar structure with interlayer of distance in the anhydrous state of from 7.9 Å to 8.2 Å and a surface area of from 9 to 20 $m^2/g$.

2. Zirconium phosphate according to claim 1 which upon hydration shows an increase of the interlayer distance, which reaches the value of 10.1 Å under conditions of relative humidity of 92%.

3. A method for the preparation of the zirconium phosphate according to claim 1 comprising (1) intercalating, into crystalline zirconium phosphate $\alpha$-$Zr(HPO_4)_2 \cdot H_2O$ having interplanar distance of 7.6 Å, an organic substance containing a proton-acceptor group and water until a stable colloidal aqueous suspension of intercalated zirconium phosphate is prepared, (2) treating the colloidal suspension with ultrasounds, (3) thereafter treating the suspension with non-zirconium-complexing acid until a precipitate of zirconium acid phosphate with modified lamellar structure is formed, (4) recovering the precipitate and washing it with dilute acid and/or water.

4. A method according to claim 3 wherein the acids are mineral acids.

5. A method according to claim 4, wherein the mineral acids are selected from HCl, $H_2SO_4$ and $HNO_3$.

6. A method according to claim 3, wherein the acid treatment of the colloidal suspension is carried out at a pH of from 0 to 3.

7. A method according to claim 6, wherein the pH is 1.

8. A method accoridng to claim 3, wherein the treatment with ultrasounds is continued until the optical density of the suspension remains constant.

9. A method according to claim 3, wherein the organic substance is an amine.

10. A method according to claim 9, wherein the amine is selected from methylamine and n-propylamine.

11. A method according to claim 10, wherein the intercalary amine is n-propylamine and is added in an amount ranging from 25% to 75% of the number of gramatoms of the acidic protons present in the amount of zirconium phosphate $\alpha$-$Zr(HPO_4) \cdot H_2O$ used.

12. A method according to claim 11, wherein the intercalary n-propylamine is added in an amount equal to 50% of the number of gram-atoms of the acidic protons present in the zirconium phosphate.

13. A method according to claim 3, wherein the stale colloidal aqueous suspension of intercalated zirconium phosphate is obtained by first intercalating the zirconium phosphate in a non-aqueous medium, and then dispersing it in water.

14. A method according to claim 13, wherein the zirconium phosphate is intercalated with n-propylamine.

15. A method according to claim 13, wherein the non-aqueous medium is an alcohol.

16. A method according to claim 15, wherein the alcohol is methanol.

17. A method according to claim 3, wherein zirconium phosphate with modified lamellar structure is recovered by filtration.

18. A method according to claim 3, wherein zirconium phosphate with modified lamellar structure is dried after the recovery and washing with dilute acid and/or water.

19. A method according to claim 18, wherein the drying is carried out in air at room temperature.

20. A method according to claim 18, wherein the drying is carried out in an oven.

21. A method according to claim 18, wherein the drying is carried out by spray-drying.

22. A method according to claim 18, wherein the drying is carried out by freeze-drying.

23. A process comprising the step of intercalating proton-acceptor organic substances having molecular weights up to 500 Daltons, wherein the zirconium phosphate according to claim 1 is the intercalan.

24. A process for recovering $Cs^+$ and $Ba^{++}$ ions by ion exchange, wherein the zirconium phosphate according to claim 1 or 2 is the ion exchanger.

25. A process comprising the step of using the zirconium phsophate according to claim 1 or 2 as a catalyst or catalyst support.

* * * * *